(12) United States Patent
Ziehmer

(10) Patent No.: US 9,101,437 B2
(45) Date of Patent: Aug. 11, 2015

(54) MANDIBULAR ATTACHMENT FOR CORRECTION OF MALOCCLUSION

(71) Applicant: T. Richard Ziehmer, Tucson, AZ (US)

(72) Inventor: T. Richard Ziehmer, Tucson, AZ (US)

(*) Notice: Subject to any disclaimer, the term of this patent is extended or adjusted under 35 U.S.C. 154(b) by 2 days.

(21) Appl. No.: 14/098,307

(22) Filed: Dec. 5, 2013

(65) Prior Publication Data

US 2014/0242534 A1 Aug. 28, 2014

Related U.S. Application Data

(63) Continuation-in-part of application No. 13/777,866, filed on Feb. 26, 2013.

(51) Int. Cl.
| | |
|---|---|
| *A61C 7/10* | (2006.01) |
| *A61C 7/36* | (2006.01) |
| *A61C 7/28* | (2006.01) |
| *A61C 7/18* | (2006.01) |

(52) U.S. Cl.
CPC . *A61C 7/36* (2013.01); *A61C 7/282* (2013.01); *A61C 7/10* (2013.01); *A61C 7/18* (2013.01)

(58) Field of Classification Search
CPC ............ A61C 7/36; A61C 7/282; A61C 7/18; A61C 7/10
USPC ............................... 433/17, 18, 19, 21, 22, 23
See application file for complete search history.

(56) References Cited

U.S. PATENT DOCUMENTS

| | | | |
|---|---|---|---|
| 4,618,324 A | 10/1986 | Nord | |
| 4,969,822 A | 11/1990 | Summer | |
| 5,352,116 A * | 10/1994 | West | 433/19 |
| 5,435,721 A | 7/1995 | Vogt | |
| 5,651,672 A | 7/1997 | Cleary et al. | |
| 5,697,782 A | 12/1997 | Klapper et al. | |
| 5,711,667 A | 1/1998 | Vogt | |
| 5,718,576 A * | 2/1998 | Schnaitter et al. | 433/22 |
| 5,752,823 A | 5/1998 | Vogt | |

(Continued)

FOREIGN PATENT DOCUMENTS

| | | |
|---|---|---|
| CA | 2608247 | 4/2009 |
| DE | 195 26 474 A1 * | 1/1997 |

(Continued)

OTHER PUBLICATIONS

LPI; "Flex Developer, Adjustable Power Developer Variable Length and Force", Flex Developer Flyer; Dec. 5, 2012, pp. 2.

(Continued)

*Primary Examiner* — Ralph Lewis
(74) *Attorney, Agent, or Firm* — Michael J. Curley; Quarles & Brady LLP

(57) ABSTRACT

Mandibular attachment structure for use in an orthodontic assembly having a force member connecting the mandibular and maxillar portions of the assembly and method of using the same. The structure includes bands dimensioned to encircle corresponding lower molars on opposite sides of the tongue, and threadless couplers each of which is removably or releasably affixed to a buccal side of a corresponding band. Neither the structure nor the method requires the use of an orthodontic brace to maintain a pressing connection between the structure and the rest of an orthodontic assembly, but the use of orthodontic braces is accommodated. The pressing connection is maintained by cooperating a hook at the end of the force member and a hook at the end of a threadless coupler.

13 Claims, 8 Drawing Sheets

(56) References Cited

U.S. PATENT DOCUMENTS

| | | | |
|---|---|---|---|
| 5,897,313 A | 4/1999 | Cleary et al. | |
| 5,964,588 A | 10/1999 | Cleary | |
| 5,980,247 A | 11/1999 | Cleary | |
| 6,053,730 A | 4/2000 | Cleary | |
| 6,113,390 A | 9/2000 | Sirney et al. | |
| 6,120,289 A * | 9/2000 | Cleary et al. | 433/22 |
| 6,168,430 B1 | 1/2001 | Higgins | |
| 6,183,250 B1 * | 2/2001 | Kanno et al. | 433/17 |
| 6,322,357 B1 | 11/2001 | Vogt | |
| 6,328,562 B1 * | 12/2001 | Sirney et al. | 433/19 |
| 6,334,771 B1 | 1/2002 | Liou | |
| 6,394,799 B1 * | 5/2002 | Testa et al. | 433/19 |
| 6,558,160 B2 | 5/2003 | Schnaitter et al. | |
| 6,589,051 B2 | 7/2003 | Cleary | |
| 6,626,665 B1 * | 9/2003 | Keles | 433/18 |
| 6,669,474 B2 | 12/2003 | Vogt | |
| 6,913,460 B2 | 7/2005 | Cleary et al. | |
| 6,988,888 B2 | 1/2006 | Cleary | |
| 2007/0026357 A1 | 2/2007 | Farber | |
| 2009/0035715 A1 | 2/2009 | Cleary | |

FOREIGN PATENT DOCUMENTS

| | | |
|---|---|---|
| DE | 103 46 489 A1 * | 8/2004 |
| WO | 2012018648 A1 | 2/2012 |

OTHER PUBLICATIONS

Proff, et al.; A Michigan-Type Occlusal Splint Wit Hspring-Loaded Mandibular Protrusion Funcationality for Treatment for Anterior Disk Dislocation with Reduction, Annuals of Anatomy; Feb. 20, 2007; pp. 362-366.

* cited by examiner

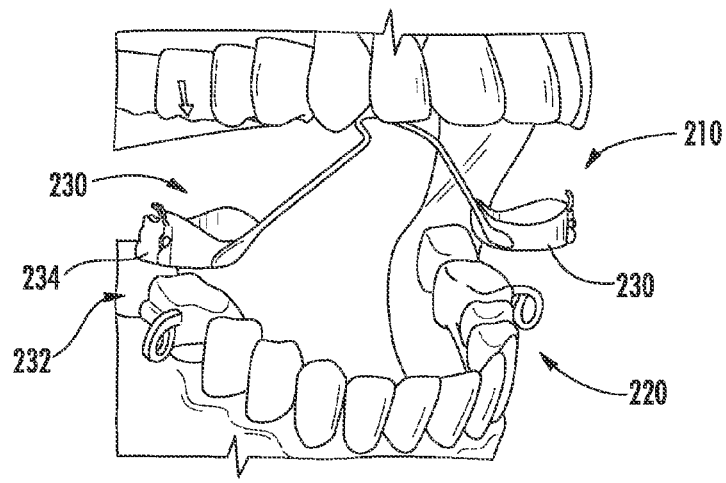
FIG. 2A
(PRIOR ART)
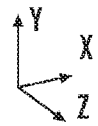
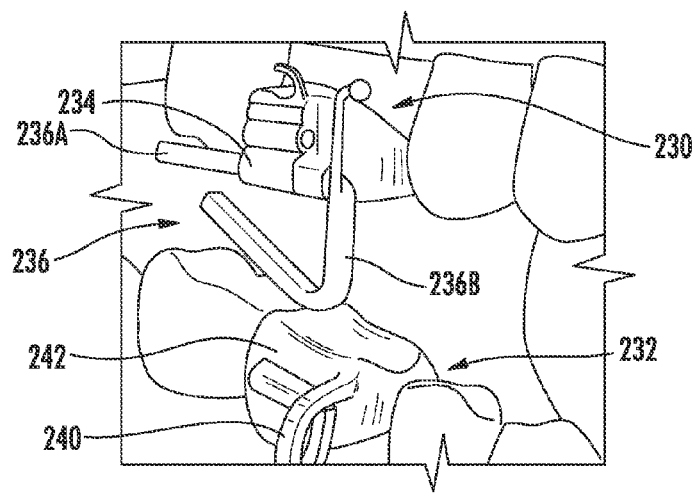
FIG. 2B
(PRIOR ART)
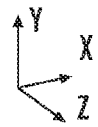
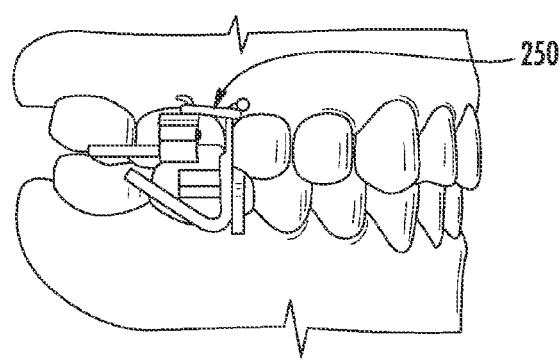
FIG. 2C
(PRIOR ART)
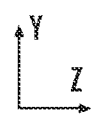

MANDIBULAR ATTACHMENT FOR CORRECTION OF MALOCCLUSION

RELATED APPLICATIONS

This application is a Continuation-in-Part of U.S. patent application Ser. No. 13/777,866 filed on Feb. 26, 2013, entitled "Mandibular Attachment for Correction of Malocclusion". The disclosure of the above-identified patent application is incorporated by reference herein in its entirety.

TECHNICAL FIELD

The present invention is in the field of orthodontics and, more particularly, it relates to devices for correction of class II malocclusions.

BACKGROUND ART

Orthodontics is a specialized field of dentistry that involves the application of mechanical forces to urge poorly positioned or crooked teeth into correct alignment and orientation. Orthodontic procedures can be used for cosmetic enhancement of teeth, as well as medically necessary movement of teeth. The orthodontic treatment of some patients includes correction of the alignment of the upper dental arch relative to the lower dental arch. Some patient have a condition referred to as Class II malocclusion or overjet, when the lower dental arch is located an excessive distance rearward of the upper dental arch when the jaws are closed. Other patients may have an opposite condition referred to as a Class III malocclusion (or negative overjet) when the lower dental arch is located forward of the upper dental arch when the jaws are closed.

Class II and Class III malocclusions may be corrected with the use of a head-gear (the effectiveness of which is almost entirely dependent on patient's compliance) or with a force-applying system such as an intraoral force module, for example. The force-applying system, when operably installed in the patient's mouth, enables the exertion of either a pulling force or a pushing force on the upper and lower jaws to which it is attached to move the jaws towards each other or away from each other.

Some known force-applying appliances are of complicated design and usually have a spring element that, in operation, requires to be repositionably attached to an auxiliary component such as an orthodontic brace to effectuate a progressive jaw correction. Other appliances employ an elastomeric member rather than a spring element, the cooperation of which with a metallic structure attaching such element to the teeth via molding or adhesive may loose its strength over time. In yet another case, the rigid affixation between the maxillar and mandibular portions of an appliance requires the use of threads and/or pins and requires a labor-intensive initial placement on the teeth and is subject to breakage and increased treatment times. Therefore, while the advantageous use of an intraoral force module has been recognized, there are still opportunities for substantial improvements.

SUMMARY

Embodiments of the present invention provide a method for using an orthodontic assembly that contains a maxillar attachment structure, a mandibular attachment structure, and a force member. The method includes (i) securing the mandibular attachment structure in removable cooperation with lower molar teeth of the patient, and (ii) pressingly connecting the maxillar and mandibular attachment structures by threadlessly cooperating the force member to a free proximal end to exert a force onto a lower molar tooth in a direction suitable to correct Class II malocclusion condition as the patient's mouth closes. The mandibular attachment structure has first and second bands each dimensioned to surround a corresponding lower molar tooth, a single arched member the ends of which are fixedly secured to posterior sides of the bands, and first and second connector portions each fixedly secured to an anterior surface of a corresponding band at a distal end and having a free proximal end. The single arched member is disposed on a posterior side of the lower teeth and wherein free distal ends of the first and second connector portions extend towards a middle of the patient's dental arch.

Embodiments of the present invention additionally provide a mandibular attachment structure for use in an orthodontic assembly, which includes first and second bands each dimensioned to surround a corresponding lower molar tooth; and a single arched member connected at its ends to first sides of the bands and extending, when operably installed in a patient's mouth, along a lingual side of the lower teeth. The first sides of the bands are associated with the lingual side of the lower teeth. The attachment structure additionally includes first and second threadless couplers, a first end of each of which is affixed to a labial side of a corresponding band. Each of the first and second threadless coupler extends along the single arched member, and the mandibular attachment structure is devoid of an orthodontic brace.

Embodiments of the present invention also provide an improvement to an orthodontic force module for use in correcting class II and/or class III malocclusions. The orthodontic force module at hand, which is devoid of an elastomeric member, has having a maxillar attachment structure affixable to two upper molar teeth with the use of upper crown bands each substantially encircling a crown of a corresponding upper molar tooth, two lower crown bands each substantially encircling a crown of a corresponding lower molar tooth. The module also includes a coupling member enabling, in operation, a forced connection between the maxillar attachment structure and the two lower crown bands. The improvement includes a single arched member secured at its end to lingual sides of the lower crown bands, where the single arched member has a retainer clasp that enables, in operation, engagement of a premolar tooth at a lingual side thereof when the so connected single arched member is operably installed in the patient's mouth. The improvement additionally includes first and second connector portions each secured to a labial surface of a corresponding lower crown band at a distal end and having a proximal end that is enabled to threadlessly cooperate with the coupling member such that a force, created through the forced connection between the maxillar attachment structure and a lower crown band, is not applied to an orthodontic brace.

Further embodiments of the present invention also provide a removable and releasable coupler between a molar band and maxillary anchored force transmitting member. Such a coupler is usable in conjunction with a buccal tube or buccal tube assembly from which it is removable. This allows for easy installation and replacement, while maintaining a threadless connection to a force member, while at the same time accommodating braces. The coupler is used in conjunction with a molar band and a buccal tube to constitute a mandibular assembly. The use of such a mandibular assembly allows for the correction of class II malocclusions at any stage of dentition. The device according to such embodiments may be used with or without braces, and with or without a lingual bow.

Exemplary embodiments include an attachment structure for transmitting mesially directed force to a molar. The attachment structure includes a molar band dimensioned to surround a corresponding lower molar tooth and a buccal tube assembly affixed to a buccal side of the molar band. The buccal tube assembly has a lip bumper tube, and optionally, another tube to accommodate a brace arch wire. The structure also includes a coupler having a straight interface portion sized to slidingly and releasably engage a cylindrical interior volume defined by the lip bumper tube. The coupler also includes a posterior loop portion proximate to the straight interface portion, the posterior loop portion limiting the travel of the straight interface portion in a mesial direction through the lip bumper tube. The coupler also has a posterior straight portion proximate to the posterior loop portion, an offsetting portion proximate to the posterior straight portion and an anterior straight portion proximate to the offsetting portion. The coupler is terminated in a free anterior end including a posterior facing hook, which serves as an attachment means to a force transmitting member. The coupler may be secured to the buccal tube with flanges located on the posterior straight portion which engage a hook on the buccal tube when the coupler is rotated in the lip bumper tube during assembly.

BRIEF DESCRIPTION OF THE DRAWINGS

The invention will be more fully understood by referring to the following Detailed Description of Specific Embodiments in conjunction with the Drawings, of which:

FIG. 2A, is a diagram illustrating schematically a structure and cooperation of portions of M.A.R.A. orthodontic appliance.

FIG. 2B is another diagram illustrating schematically a structure and cooperation of portions of M.A.R.A. orthodontic appliance.

FIG. 2C is yet another diagram illustrating schematically a structure and cooperation of portions of M.A.R.A. orthodontic appliance.

DETAILED DESCRIPTION

Figure 1A:
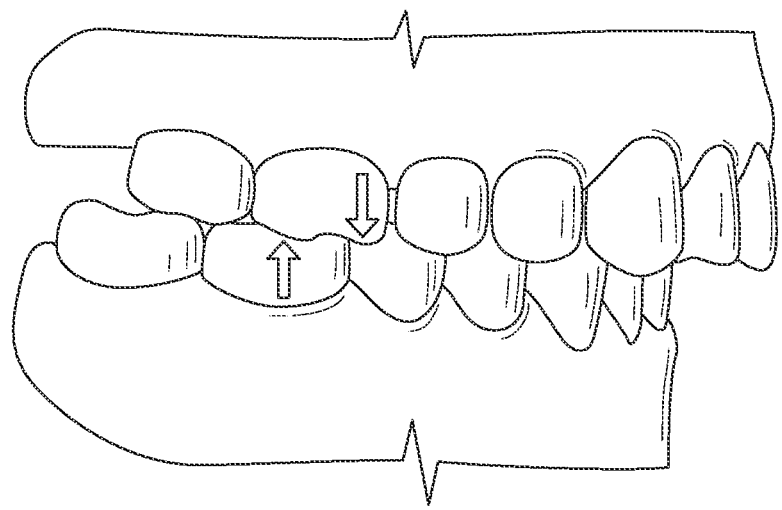
FIG. 1A illustrates Class II malocclusion
Figure 1B:
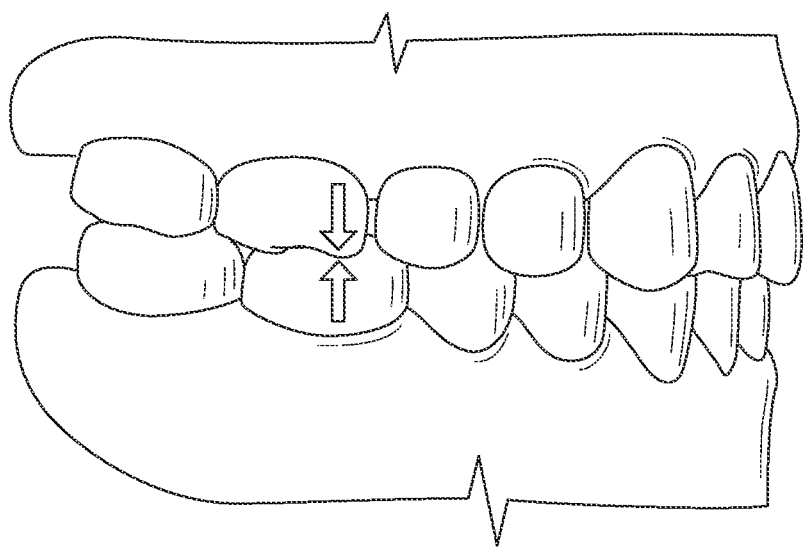
FIG. 1B illustrates Class I normal occlusion.

Class II malocclusion occurs in approximately 33% of the general population in the United States and presents a challenge for the orthodontist. In reference to FIG. 1A, Class II malocclusion occurs when the lower jaw is deficient in length and sits behind the upper jaw. Not only can this compromise proper function, but often times can be a contributing factor to a less attractive smile and profile appearance. FIG. 1B presents, for comparison, a depiction of normal occlusion (Class I). Historically, a Class II occlusion has been treated effectively with headgear appliances that are best utilized when a patient is a still-growing child. The conventional headgear serves to maintain the position of the upper jaw while the lower jaw expresses its natural growth in a forward direction, and therefore correcting the occlusion. However, the downside of the headgear appliance is that it is unattractive, and its success is entirely dependent upon patient compliance; something that has been and continues to be an ongoing problem in orthodontics.

The intra-oral force-applying appliances of related art used as alternatives to head gear have certain limitations. For example, many such devices are of complex design, requiring a number of moving parts (such as pins, for example), and cannot be easily installed in the correct location in a patient's mouth. Additionally, many intra-oral devices for occlusion correction are not easily adaptable to being employed during the period of growth spurts of the patient (ranging anywhere from as early as 8.5 years in females to as late as 14 years in males) in either the mixed dentition or permanent dentition periods. Many such devices, for example, require permanent dentition prior to installation, at which point much of a patient's growth is already over, which limits the efficacy of the devices.

Additionally, it is sometimes advantageous for such intra-oral orthodontic appliances to be configured to be independent from the usage of orthodontic braces and to enable the malocclusion correction with or without orthodontic braces placed on the patient's teeth. The orthodontic brackets and wires, which together are commonly referred to as "braces", include small slotted bodies configured to be directly attached to the patient's teeth or, alternatively, to be attached to bands which are, in turn, cemented or otherwise secured around the teeth. Once the brackets are affixed to the patient's teeth, a curved wire is inserted into the bracket slots. The brackets and the arch wire cooperate to guide corrective movement of the teeth into proper alignment. Typical corrective movement provided by the braces include torque, rotation, and leveling of the teeth. An example of orthodontic appliance that cannot be used at the same time when a patient wears orthodontic braces prescribed by the dentist is provided by the so-called Higgins Crossbow appliance that requires the use of two arched members one of which is extended along the labial side of the teeth where an orthodontic bracket would be placed. Other appliance, such as the Forsus appliance, discussed in more detail below, require the installation of braces for use.

To illustrate some devices of related art, FIGS. 2A, 2B and 2C provide diagrams of components of the M.A.R.A. appliance, showing the maxillar and mandibular portions 210, 220 fixed on molar teeth of the upper and lower molar teeth, respectively, with crowns 230, 232. While FIGS. 2A, 2B offer perspective views of the appliance attached to teeth in the open mouth of the patient, FIG. 2C illustrates a substantially side view of the mouth that is equipped with the appliance and the jaws of which are closed. To form a connection between the upper and lower jaws, when the patient's mouth is closed, the crown 230 of the maxillar portion 210 is equipped with a tube bracket 234 that is dimensioned to removably accept a pin 236 having a first portion 236A insertable into a hollow of the bracket 234 and a second portion 236B extended transversely to the first portion 236A. The crown 232 of the mandibular portion 220, in turn, is fixedly equipped with a stopper 240 extending and defined in a surface (substantially corresponding to the xy-plane of FIG. 2C) that is transverse to a labial surface 242 of the crown 232 to provide support to which, as shown in FIG. 2C, the second portion 236B of the pin 236 is pressed and against which the second portion 236B applies force in operation. While this appliance can be employed in the mixed or permanent dentition and with or without braced placed on the teeth, the outward extension of the stopper 240 from a tooth toward a lip of the mouth and a need to secure the pin 236 in a tube bracket 234 (for example with a rubber band 250, as shown in FIG. 2C) unnecessarily complicate its practical use.

Figure 3A:
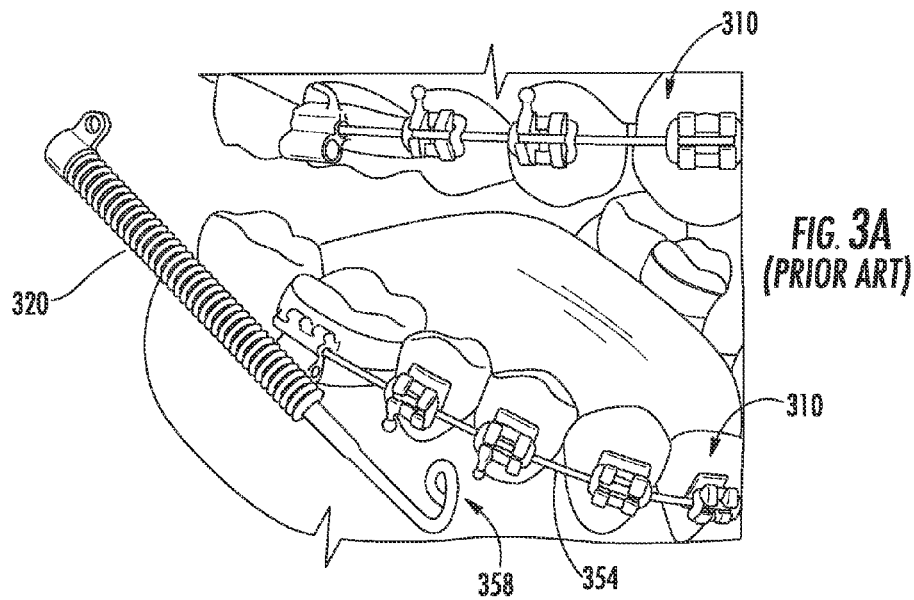
FIG. 3A is a diagram illustrating schematically a structure and cooperation of portions of Forsus orthodontic appliance.
Figure 3B:
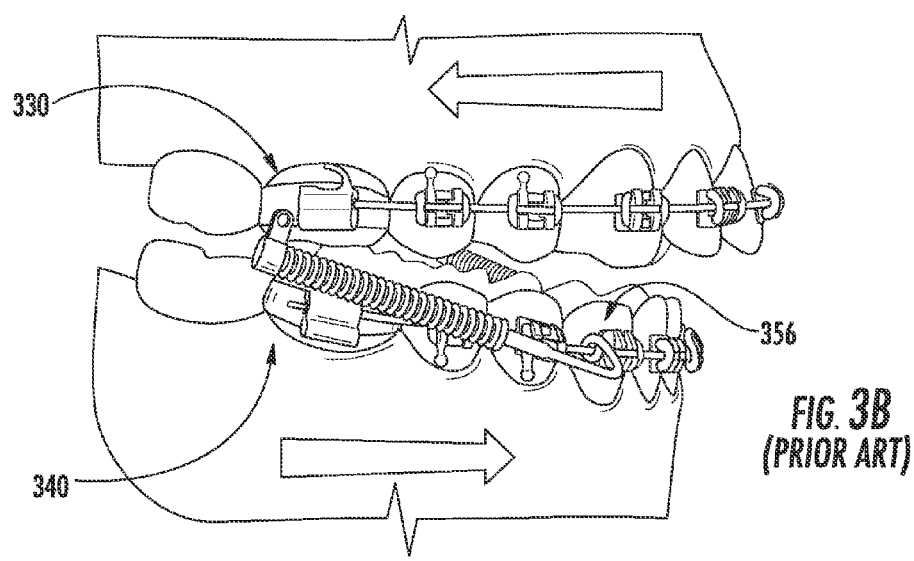
FIG. 3B is a diagram illustrating schematically a structure and cooperation of portions of Forsus orthodontic appliance.

The Forsus appliance, illustrated in diagrams of FIGS. 3A, 3B can only be used when the patient has all of his or her permanent teeth erupted and braces 310 are placed on all teeth. As shown in FIG. 3B, the spring member 320 that connects the maxillar and mandibular portions 330, 340 of the Forsus appliance, requires affixation to a wire 354 of the orthodontic brace 310 at least at one end. As shown at 356, such affixation is achieved with the use of a hook or loop 358 formed at an end of the member 320, which slides along the wire 354. (While the spring member 320 is illustrated as a coil spring, a related (not shown) structure may employ a leaf-spring or a spring structured as a bent rod.) A significant number of patients are well past their growth spurt by the time all upper and lower permanent teeth have erupted, thus limiting the amount of skeletal correction that can be achieved and rendering the current model of the Forsus appliance not particularly effective for many patients. Additionally, in operation hook or loop 358 formed at the end of member 320 of the Forsus appliance exerts force on at least one bracket of the brace 310 to which it is affixed. As a result, breakage or loss of adhesion of the brace brackets is common with the Forsus appliance, which requires frequent office visits to repair.

Embodiments of the present invention provides an orthodontic appliance that alleviates the above-identified problems and limitations of operation and enables the Class II and/or Class III malocclusion correction during the mixed dentition phase, without reliance on, or damage to, an orthodontic brace.

Referring now to FIGS. 4A through 4D, an embodiment of the invention includes a mandibular attachment structure 410 that is devoid of elastomeric material and that is affixable to the first and second lower molar teeth with the use of bands 412, 414, each of which is appropriately dimensioned to surround a corresponding lower molar tooth. According to the idea of the invention, the interconnection of the bands 412, 414 is configured on only the lingual side of the embodiment. Accordingly, the bands 412, 414 are linked with a single arched member 418 (made, in one implementation of a wire) the ends of which are securely affixed to anterior, lingual sides of the bands 412, 414. The arched member may optionally be equipped with at least one (as shown—two) retainer clasp 420 that, in operation (when the embodiment is installed into a patient's mouth), enables the engagement between the arched member 418 and a premolar tooth on its lingual side. To a labial side of each of the bands 412, 414 a corresponding connector or coupler 422, 424 is secured (for example, by soldering) that is extended along a corresponding jaw toward the middle of the patient's dental arch (labeled as 430). Portions of the connectors 422, 424 that are distal to the bands 412, 414 may be transversely offset from the bands by offset sections 432, 434, and are terminated with attachment means that are devoid of threads, such as, for example, hooks 442, 444.

The embodiment of the invention may additionally include a maxillar attachment structure 450 containing a band affixing the maxillar structure to an upper molar tooth. The embodiment may further include force member(s) 452, 454 (including, for example, a coil or leaf or rod spring) configured to be affixable to the maxillar attachment structure 450 (through, for example, a pin or clasp fitting to an appropriate receiving portion of the maxillar attachment structure such as a tube bracket or a hook) at one end and threadlessly and pinlessly cooperating with the attachment means 442, 444 of the mandibular structure 410. In operation, when both the mandibular structure 410 and the maxillar structure 450 are installed in the patient's mouth and connected to the force member(s) 452, 454, and when the patient closes his jaws, the force member(s) 452, 454 pressingly connect the structures 410 and 450 to exert a force on lower molar teeth (through the couplers 422, 432 and the bands 412, 414) in a direction suitable to correct Class II or Class III malocclusions. The force applied to the lower jaw is progressively adjustable by adjusting the tension in the force member(s) 454. In contradistinction with devices of the related art, such transfer of force does not require the presence and/or use of orthodontic braces and can be used contemporaneously with the use of these braces or at a time when the braces are not prescribed. Moreover, the fact that the attachment elements 442, 444 of the mandibular structure 410 are devoid of protrusions or excursions that are transverse to the labial side of the brackets 412, 414 improves patient's comfort in wearing such orthodontic appliance, as compared to the M.A.R.S. appliance, for example.

In one implementation, the mandibular portion 410 of the article of the invention can be used as an attachment for the Forsus arms of a portion of the Forsus appliance during the mixed dentition, thereby increasing the effectiveness of the Forsus appliance and extending its use to a greater number of patients. The method for using an orthodontic assembly according to an embodiment of the invention includes securing the mandibular attachment structure of the invention in removable cooperation with lower molar teeth of the patient such as to surround these teeth with first and second bands 412, 414 of the mandibular structure, to place the arched member 418 of the lingual side of the lower teeth and to position the connector or couplers 422, 432 on the labial side of the lower teeth with the hooks 442, 454 extending towards the middle 430 of the dental arch of the patient.

Figure 4A:
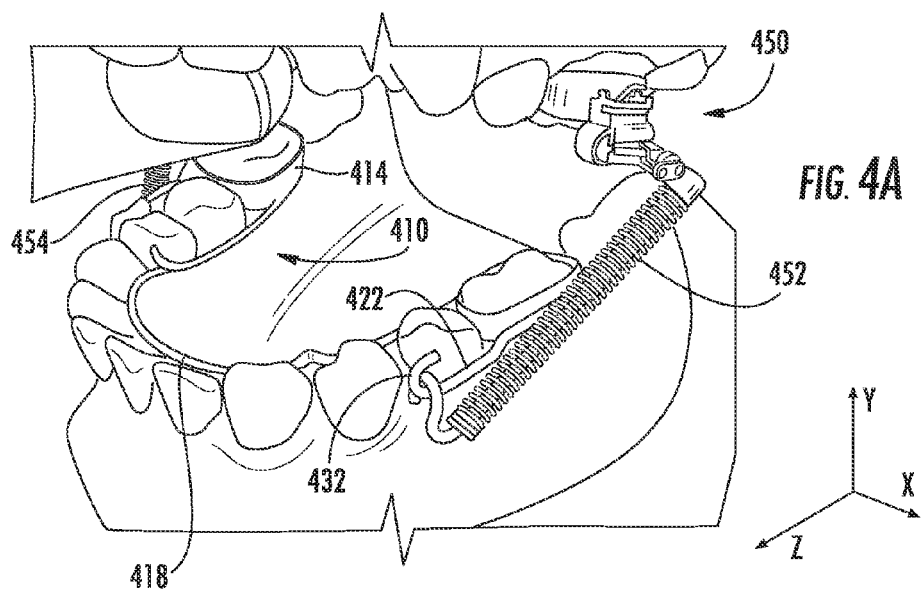
FIG. 4A is a diagram illustrating schematically a structure and cooperation of a portion of an orthodontic appliance according to an embodiment of the invention.
Figure 4B:
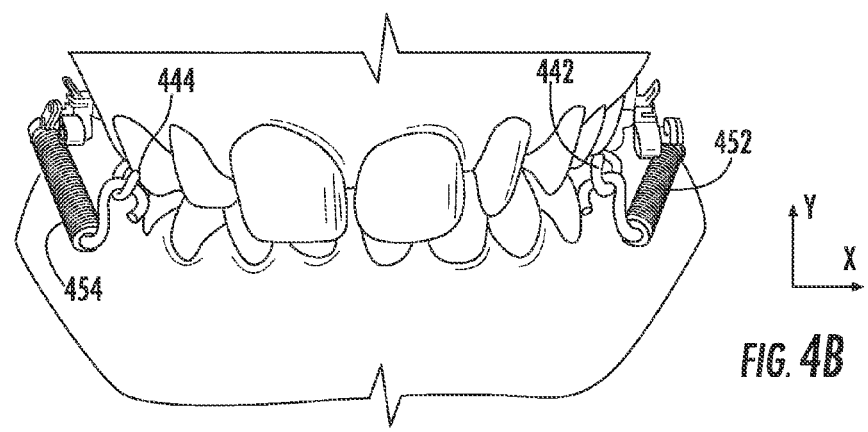
FIG. 4B is another diagram illustrating schematically a structure and cooperation of a portion of an orthodontic appliance according to an embodiment of the invention.
Figure 4C:
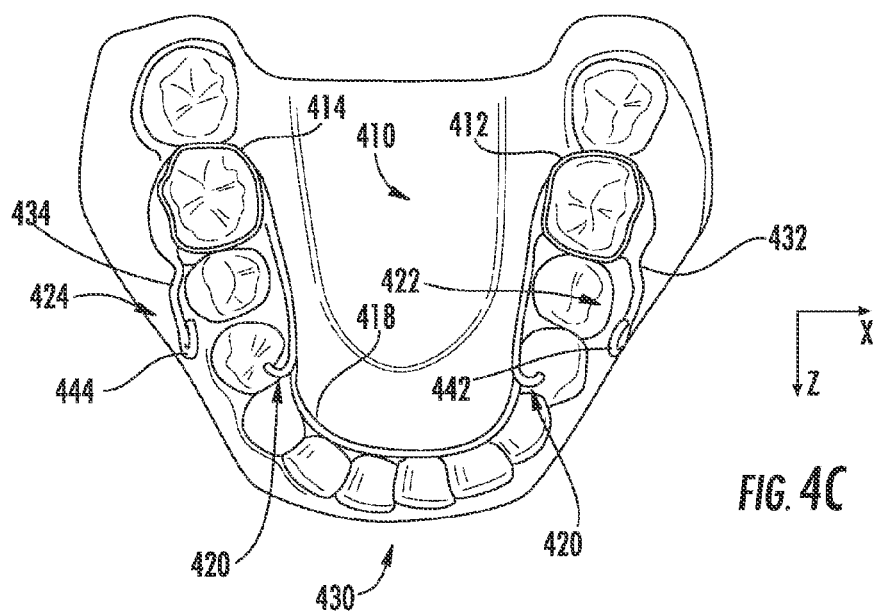
FIG. 4C is another diagram illustrating schematically a structure and cooperation of a portion of an orthodontic appliance according to an embodiment of the invention.
Figure 4D:
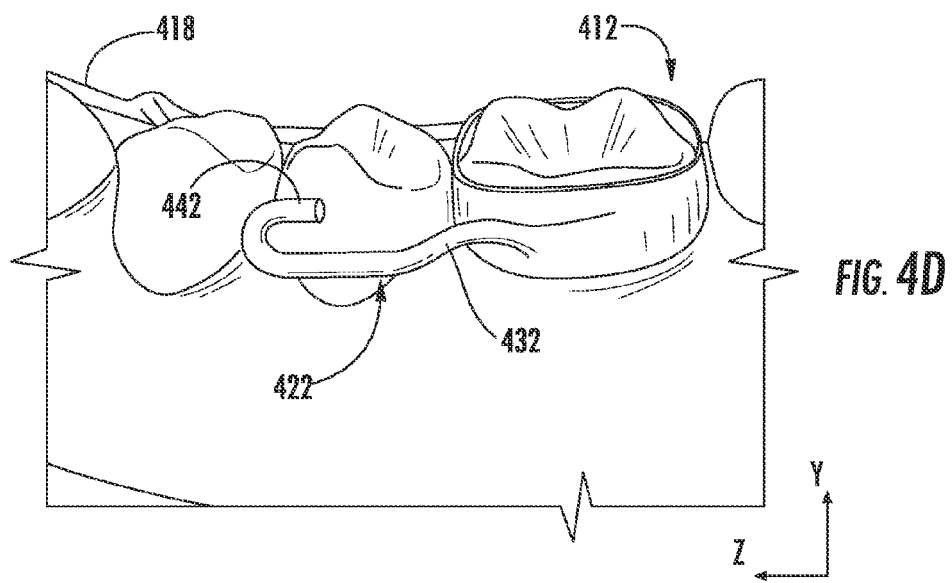
FIG. 4D is another diagram illustrating schematically a structure and cooperation of a portion of an orthodontic appliance according to an embodiment of the invention.

As can be seen in FIGS. 4C and 4D, in those embodiment, couplers 422, 424 are provided in the form of a rigid, non-compressible, non-extensible wires that terminate in attachment means, for example, posterior facing hooks 442, 444. In practice, the device of FIGS. 4C and 4D is fabricated by having a third party laboratory solder couplers 432, 434 to the corresponding molar bands. The result is that couplers 432, 434 are permanently affixed to molar bands 412, 414.

Figure 5A:
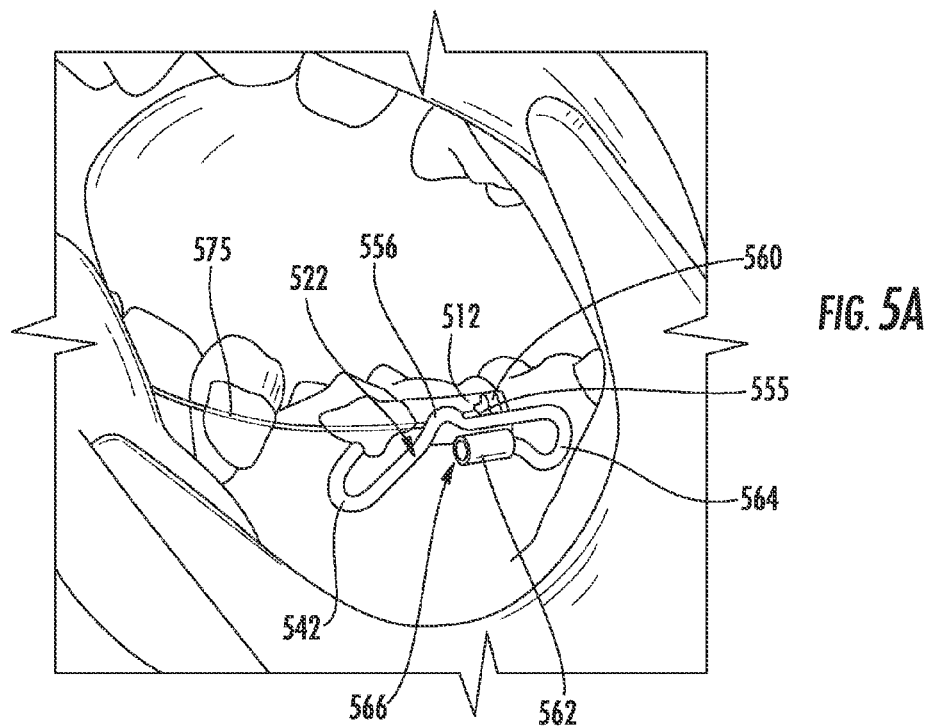
FIG. 5A is a diagram illustrating schematically structure and cooperation of a portion of an orthodontic appliance according to an embodiment of the invention.
Figure 5B:
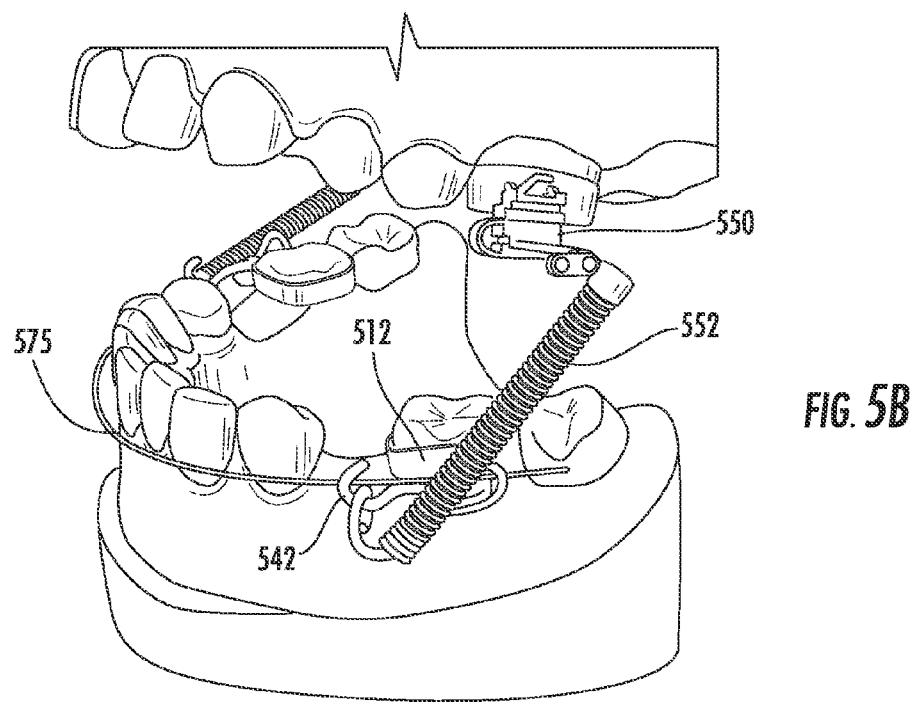
FIG. 5B is a related diagram illustrating schematically structure and cooperation of a portion of an orthodontic appliance according to an embodiment of the invention.

FIGS. 5A-F show an alternative to the arrangement of FIGS. 4A-D, which uses a removable coupler as part of the mandibular attachment structure, rather than a coupler that is permanently affixed to the molar band. As can be seen in FIG. 5A, this embodiment includes a molar bands, for example, molar band 512, which is appropriately dimensioned to surround a corresponding lower molar tooth. A buccal tube 560 is affixed to a buccal surface of molar band 512. As will be described in additional detail in relation to FIG. 5C, buccal tube 560 includes a tubular portion 562, which defines a cylindrical volume with the long axis of the cylindrical volume being oriented in a mesial direction. Coupler 522 is provided, which has a posterior loop portion 564, which includes an anterior facing loop, and a straight interface portion 566 sized to slidingly engage the interior surface of the tube portion 562 of buccal tube 560. Coupler 522 includes a serpentine offsetting portion 556, which provides for clearance between coupler 522 and the canine and pre-molar, if necessary, depending on the length of coupler 522. Coupler 522 includes a free anterior end, which forms an attachment means 542. In the arrangement of FIG. 5A, attachment means 542 is arranged as a backward or posterior opening or facing hook. In certain installations, the use of molar band 512 in conjunction with buccal tube 560 enables the device to optionally be used in conjunction with brace arch wire 575, which may be affixed to another tube or slot defined by buccal tube 560. In practice, as in the embodiment of FIGS. 4A-D, the device of FIG. 5A is used in a pair, as is shown in FIG. 5B. A pair of molar bands according to the arrangement of FIGS. 5A and 5B may optionally be joined by a non-illustrated lingual bow, such as arch member 418 described above. However, it is important to note that there may be advantages to omitting the lingual bow 418, which are described more fully below. Both the use of a lingual bow, and the absence of a lingual bow are within the scope of the invention.

FIG. 5B illustrates the interface of the device of FIG. 5A with a force transmitting device or member, such as a Forsus appliance. As in the arrangement described above with respect to FIG. 4A, a maxillar attachment structure 550 containing a band affixing the maxillar structure to an upper molar tooth is provided. A force member 552 (including, for example, a coil or leaf or spring loaded telescoping rod) is provided which is configured to be affixable to the maxillar attachment structure 550 (through, for example, a pin or clasp fitting to an appropriate receiving portion of the maxillar attachment structure such as a tube bracket or a hook) at one end. The force member threadlessly and pinlessly cooperates with the attachment means 542 of the coupler 522. In operation, when both the mandibular structure (shown in FIG. 5A) and the maxillar structure 550 are installed in the patient's mouth and connected to the force member 552, and when the patient closes his jaws, the force member 552 pressingly connects the structures 550 and the structures of FIG. 5A, to exert force on the lower molar (through the coupler 522 and the molar band 512) in a direction suitable to correct Class II malocclusions. In this embodiment, the force applied to the lower jaw is progressively adjustable by adjusting either or both of the tension in the force member(s) 552 and/or the length of the coupler 522.

Figure 5C:
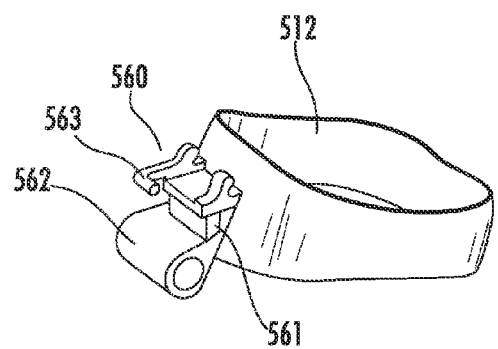
FIG. 5C is a related diagram illustrating schematically structure and cooperation of a portion of an orthodontic appliance according to an embodiment of the invention.
Figure 5D:
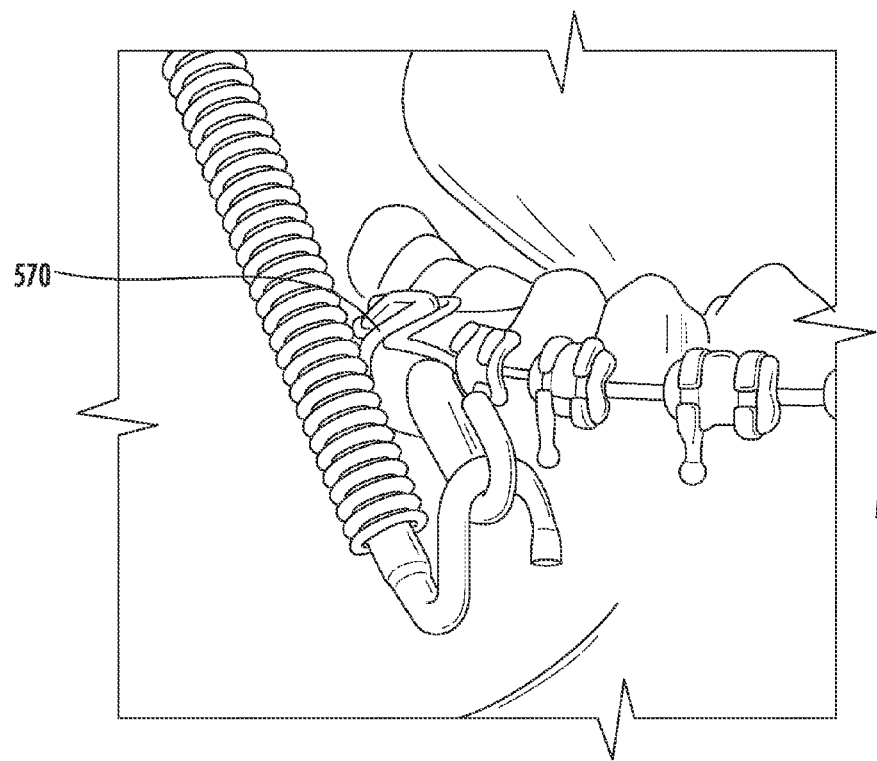
FIG. 5D is a related diagram illustrating schematically structure and cooperation of a portion of an orthodontic appliance according to an embodiment of the invention.

FIG. 5C shows a mandibular structure (i.e., a molar band affixed to a buccal tube) of one embodiment of the invention in greater detail. As can be seen in FIG. 5C, a mandibular attachment or anchor structure includes a molar band 512 sized to fit over, for example, a patient's first molar. Affixed on a buccal side of the molar band 512 is a buccal tube or buccal tube assembly 560. In the embodiment of FIG. 5C, buccal tube 560 is a double tube that defines a first tube or channel 561 and a second tube 562 to a buccal or outside side of the first tube 561. Second tube 562 may be a "lip bumper tube". First tube 561 is optionally usable for passage or anchoring of a brace arch wire, such as 575. Both tubes 561, 562 define closed channel regions that are oriented along an axis parallel to an axis extending in the mesial direction. Buccal tube 560 also includes a hook 563, which along with second tube 562, is used to locate, orient and anchor a coupler, such as coupler 522 described above.

As is set forth in more detail below with respect to FIGS. 5E and 5F, coupler 522 is releasably or removably joined to buccal tube 560 by sliding straight interface portion 566 of coupler 522 into the second tube 562 such that substantially the entirety of the straight interface portion 562 overlaps with the second tube 562. When this step is performed, the coupler is clocked such that loop of posterior loop portion 564 is disposed in the plane of the mandibular teeth. In other words, during installation, the coupler 522 is rotated 90 degrees from the final installed orientation that is depicted in FIG. 5A. Beyond the straight interface portion 566 (i.e., posterior of straight interface portion), coupler 522 includes a posterior loop portion 564 which interferes with further passage of the straight interface portion 566 of the coupler as it is slid into the second tube 562 in a mesial or anterior direction. Thus, once the coupler "bottoms out" (i.e., once the transition zone between the straight interface portion 566 and the posterior loop portion 564 interferes with continued forward passage of the straight interface portion 566 into the second tube 562), the coupler 522 is releasably anchored to the buccal tube 560 by rotating coupler 522 about the long axes of the second tube 562/straight interface portion 566, until it is in the orientation depicted in FIG. 5A. One or more flanges 555 are disposed on the surface of coupler in a straight region posterior to the serpentine offsetting portion 556. Upon rotation of the coupler 522 into the installed orientation of FIG. 5A, these flanges 555 engage hook 563 to secure coupler 522 to buccal tube 560. For additional security, an elastic band 570 or stainless steel ligature tie may be placed in the manner shown in FIG. 5D.

Figure 5E:
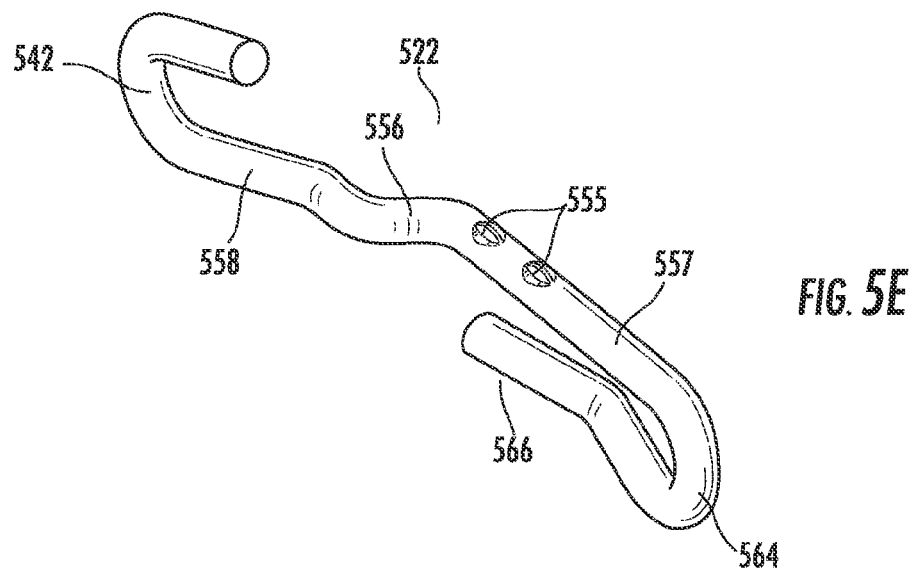
FIG. 5E is another diagram illustrating schematically, in perspective view, structure and cooperation of a portion of an orthodontic appliance according to an embodiment of the invention.
Figure 5F:
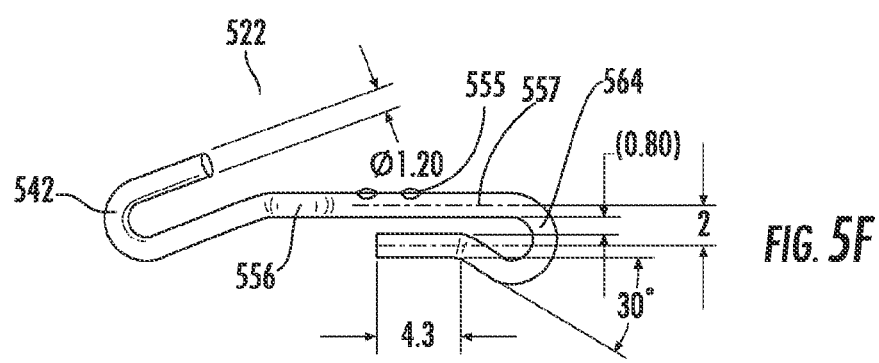
FIG. 5F is a side view of the portion of FIG. 5E illustrating schematically structure and cooperation of a portion of an orthodontic appliance according to an embodiment of the invention.
Figure 5G:
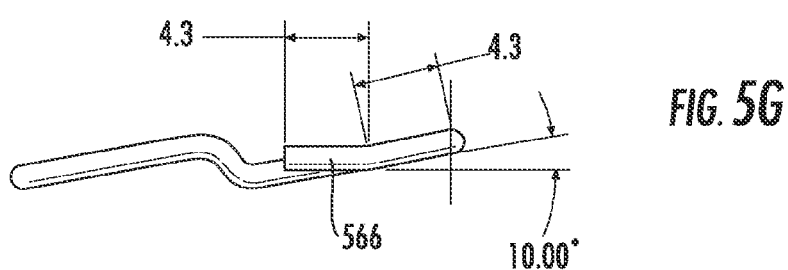
FIG. 5G is a top view of the portion of FIG. 5E illustrating schematically structure and cooperation of a portion of an orthodontic appliance according to an embodiment of the invention.

FIGS. 5E, 5F, and 5G illustrate coupler 522 in additional detail. In one exemplary embodiment, coupler 522 is fabricated from a single piece of 1.2 mm diameter stainless steel wire. Coupler 522 has a straight interface portion 566, which transitions to a posterior loop portion 564, which defines an anterior-facing loop. Posterior loop portion 564 transitions to a posterior straight portion 557, into or onto which are disposed one or more flanges 555. Straight interface portion 566 and posterior straight portion 557 are not co-planar, rather, in one exemplary embodiment, there is a 10 degree angle between the axes of these straight portions. Because buccal tube 560 (and more particularly, second tube 562) captures straight interface portion 566, the effect of this 10 degree offset angle is that when installed, coupler 522 is angled away from the buccal surfaces of the adjacent teeth. Posterior straight portion transitions through serpentine offsetting portion 556 to an anterior straight portion 558, which then transitions to attachment means 542. In the embodiment of FIGS. 5A-5G, attachment means 542 is realized as a posterior facing loop or hook. While the loops of attachment means 542 and posterior loop portion 564 are arranged in parallel planes, they are not co-planar because serpentine offsetting portion 556 serves to introduce an offset in the planes in which these loops are defined. In the embodiment of FIGS. 5F-5G, this offset is 2 millimeters.

The removable hook coupler 522 described above provides the clinician and patient with many advantages over the embodiment of FIG. 4, as well as conventional appliances, such as the Herbst and Higgins Cross Bow appliances. One advantage is that the device of FIG. 5 can be used during any stage of the dentition, with or without braces placed on the patient, and can even be placed without having to be sent to a laboratory first. In addition, it is the only class II functional appliance that has the ability to close space in the mandibular arch by mesializing the first molar and second premolar without distalizing any of the mandibular anterior teeth.

The Higgins Cross Bow appliance cannot be placed on patients who have mandibular braces due to the interference that would take place between the braces and the labial bow on the Higgins Cross Bow appliance. When the clinician is trying to achieve class II correction at a relatively early stage this is not an issue because the patient usually is not fitted with mandibular braces. Often times, however, a patient doesn't present to an office until all the permanent teeth have erupted, which results in the both the clinician and patient wanting to expedite treatment by trying to align all teeth and get class II correction at the same time. This situation excludes the Higgins Cross Bow appliance from being used and leaves only the traditional Forsus appliance, Herbst appliance (special version), or class II elastics for class II correction.

However, the device of FIG. 5 has advantages over those conventional solutions. The Herbst appliance requires lab fabrication, is very bulky, and has a high breakage rate. The Forsus appliance is easy to place but attaches directly to the mandibular archwire and presses against either the distal surface of the mandibular first bicuspid bracket or the distal of the mandibular canine bracket, which can be seen in FIG. 3B. Because of the significant force the Forsus rod applies it often results in broken mandibular first bicuspid and canine brackets, which can significantly increase treatment times. Class II elastics only provide a minimal amount of molar correction due to their limited force and only when the patient fully complies with instructions, which almost never happens.

In contrast, the removable coupler of FIG. 5, can be placed at anytime during treatment with braces and only requires clinicians use a mandibular first molar band with a lip bumper tube attachment. The coupler 522 is designed such that the retention bumps or flanges 555 on the hook will snap into the buccal tube hook 563 when inserted into the distal end of the lip bumper tube at an angle of approximately 90 degrees away from the buccal tube and then rotated 90 degrees toward the buccal tube and into its final upright position (shown in FIG. 5A). After securing the hook in with a 0.012" stainless steel ligature tie the clinician or orthodontic technician simply places the Forsus rod directly onto the coupler, bypassing the wire and braces and thereby eliminating the chance of breaking brackets while the Forsus rod is in use.

Another advantage of the device of FIG. 5 is the ability to utilize the Forsus Appliance along with the removable coupler 522 in order to achieve class II correction and close mandibular space. No other appliance known to the applicant can achieve similar correction. Because, in certain embodiments, there is no soldered lingual bar (e.g., 418) on the mandibular first molar band that rests against the lingual surface of the mandibular anterior teeth, the mandibular molar tooth can move forward (mesial) when the Forsus appliance (or any other force member) is attached. The Herbst appliance, Higgins Cross Bow appliance, in contrast, all have soldered lingual bars that prevent any space closure.

There are many class II, crowding cases where the clinician will extract the maxillary first bicuspid teeth as well as the mandibular second bicuspid teeth in order to alleviate crowding in both arches and correct a class II molar relationship. Traditional methods involve using class II elastics, but as mentioned above, such conventional treatments come with many limitations and rely solely on patient compliance. The Forsus Appliance along with the removable coupler of FIG. 5 provides superior class II correction and mandibular space closure with minimal breakage and easy installation.

While the invention is described through the above-described exemplary embodiments, it will be understood by those of ordinary skill in the art that modifications to, and variations of, the illustrated embodiments may be made without departing from the inventive concepts disclosed herein. Furthermore, disclosed aspects, or portions of these aspects, may be combined in ways not listed above. Accordingly, the invention should not be viewed as being limited to the disclosed embodiment(s).

What is claimed is:

1. A method for using an orthodontic assembly including a maxillar attachment structure, a mandibular attachment structure, and a force member, the method comprising:
   securing the mandibular attachment structure in removable cooperation with lower molar teeth of the patient,
      the mandibular attachment structure having
         first and second bands each dimensioned to surround a corresponding lower molar tooth,
         first and second buccal tube assemblies, each defining a buccal tube and a buccal hook, the buccal tube assemblies affixed to a buccal side of a corresponding of the first and second bands, and
         first and second couplers, each coupler having
            a free mesial end, and
            a distal end defining a distal hook a straight interface portion of which is releaseably engaged in a corresponding of the first and second buccal tubes,
   securing the maxillar attachment structure to upper molar teeth with the use of upper crown bands; and
   pressingly connecting the maxillar and mandibular attachment structures by affixing one end of the force member to the maxillar attachment structure and threadlessly cooperating another end of the force member to a free mesial end of a corresponding coupler to exert a force from the maxillar attachment onto a lower molar tooth in a direction suitable to correct Class II malocclusion condition as the patient's mouth closes,
   wherein each coupler further includes at least one flange, between distal and mesial ends of said coupler, arranged to releaseably engage a corresponding buccal hook as said coupler is rotated about a long axis of its straight interface portion when the straight interface portion is seated in a corresponding buccal tube.

2. The method according to claim 1, further comprising maintaining the pressing connection between the maxillar and mandibular attachment structures without the use of an orthodontic brace.

3. The method according to claim 1, further comprising maintaining the pressing connection between the maxillar and mandibular attachment structures with the use of an orthodontic brace wire anchored to the first and second buccal tubes.

4. The method according to claim 1, wherein the securing the mandibular attachment structure includes securing the mandibular attachment structure in which a free mesial end of each coupler is bent to form an attachment hook and wherein the pressingly connecting includes cooperating a hook at an end of the force member with the attachment hook.

5. The method according to claim 4, wherein the securing the mandibular attachment structure includes securing the mandibular attachment structure in which the attachment hooks of the first and second free mesial ends of the first and second couplers are formed in planes extending substantially along buccal surfaces of the first and second bands.

6. The method of claim 1, wherein the securing the mandibular attachment structure includes securing the mandibular attachment structure in which a coupler includes a serpentine offsetting portion which offsets a plane in which a distal hook of said coupler is defined from a plane in which said attachment hook at the free mesial end of said coupler is defined.

7. The method according to claim 1, wherein the securing the maxillar attachment structure includes securing the maxillar attachment structure that includes a maxillar anchor band, and wherein the force member includes a spring-loaded telescoping rod terminating in a hook.

8. The method according to claim 1, wherein
the securing the mandibular attachment structure includes securing the mandibular attachment structure in which each coupler has an attachment hook at its mesial end, and wherein a first plane defined by said attachment hook and a second plane defined by a distal hook of said coupler are parallel to one another.

9. The method of claim 8, wherein the securing the mandibular attachment structure includes securing the mandibular attachment structure in which the couplers are further releaseably affixed to their respective buccal tubes using elastic bands connecting the couplers to the buccal tubes.

10. An attachment structure for transmitting mesially directed force to a molar, comprising:
a molar band dimensioned to surround a corresponding lower molar tooth;
a buccal tube assembly affixed to a buccal side of the molar band, the buccal tube assembly defining a buccal tube;
a coupler having a straight interface portion sized to slidingly and releaseably engage a cylindrical interior volume defined by the buccal tube,
wherein the coupler also comprises
a posterior loop portion proximate to the straight interface portion, the posterior loop portion limiting the travel of the straight interface portion in a mesial direction through the buccal tube;
a posterior straight portion proximate to the posterior loop portion;
an offsetting portion proximate to the posterior straight portion;
an anterior straight portion proximate to the offsetting portion, and
a free anterior end including a posteriorly facing hook, which serves as an attachment means to a force transmitting member,
wherein the buccal tube assembly further includes a buccal hook, and
wherein the posterior straight portion of the coupler includes at least one flange arranged to releaseably engage the buccal hook when the straight interface portion of the coupler is rotated within the buccal tube such that the posteriorly facing hook of the free anterior end is contained in a plane transverse to a plane containing an entire circumference of the molar band.

11. The attachment structure of claim 10, wherein the posterior loop portion defines an anteriorly facing loop.

12. The attachment structure of claim 11, wherein the offsetting portion offsets a plane containing the anteriorly facing loop from a plane containing the posteriorly facing hook.

13. The attachment structure of claim 11, wherein a plane containing a long axis of the straight interface portion makes a non-zero angle with a plane containing the anteriorly facing loop.

* * * * *